(12) United States Patent
Counsell et al.

(10) Patent No.: US 6,417,384 B1
(45) Date of Patent: Jul. 9, 2002

(54) RADIOIODINATED PHOSPHOLIPID ETHER ANALOGS AND METHODS OF USING THE SAME

(75) Inventors: Raymond E. Counsell; Marc A. Longino; Anatoly N. Pinchuk, all of Ann Arbor, MI (US); Mark A. Rampy, Gaithersburg, MD (US); Jamey P. Weichert, Fitchburg, WI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/898,178

(22) Filed: Jul. 3, 2001

Related U.S. Application Data

(62) Division of application No. 09/319,406, filed on Sep. 20, 1999, now Pat. No. 6,255,519.

(30) Foreign Application Priority Data

Apr. 12, 1999 (WO) .................................. PCT/US96/19352

(51) Int. Cl.$^7$ .................................................. C07F 9/10
(52) U.S. Cl. ........................ 558/166; 558/169; 424/9.37
(58) Field of Search ................... 558/116, 169

(56) References Cited

U.S. PATENT DOCUMENTS

| | | |
|---|---|---|
| 4,925,649 A | 5/1990 | Counsell et al. |
| 4,965,391 A | 10/1990 | Counsell et al. |
| 5,087,721 A | 2/1992 | Counsell et al. |
| 5,347,030 A | 9/1994 | Counsell et al. |

OTHER PUBLICATIONS

Akiyama et al., "AlCl,–N,N–dimethylamiline: A Novel Benzyl and Allyl Ether Cleavage Reagent," *Bull. Chem. Soc., Jpn.* 65:1932–1938 (1992).

Fouquent and Schlosser, "Improved Carbon–Carbon Linking by Controlled Copper Catalysis," *Agnew. Chem. Int. Ed.* 13:82–83 (1974).

Kotting et al., "Alkylphosphocholines; Influence of Structural Variation on Biodistribution at antineoplastically Active Concentrations," *Cancer Chemother. Pharm.* 30:105–112 (1992).

Pienta et al., Inhibition of Spontaneous Metastasis in a Rat Prostate Cancer Model by Oral Administration of Modified Citrus Pectin, *J. Natl. Cancer Inst.* 87:348–353 (1995).

Rampy et al., "Synthesis and Biological Evaluation of Radio–Iodinated Phospholipid Ether Analogs," *Nucl. Med. Biol.* 22:505–512 (1992).

Schlosser and Bossert, "The 'Two–Fold Reaction' Benchmark Applied to the Copper Catalyzed Assembling of 1,ω–difunctional Hydrocarbon Chains," *Tetrahedron* 47:6287–6292 (1991).

Tayck et al., Influence of the Walker 256 Carcinosarcoma on Muscle, Tumor, and Whole–Body Protein Synthesis and Growth Rate in the Cancer–Bearing Rat, *Cancer Res.* 46:5649–5654 (1986).

Weichert et al., "Radioiodination Via Isotope Exchange in Pivalic Acid," *Appl. Radiat. Isot.* 37:907–913 (1986).

Choyke, "Imaging of prostate cancer," Abdom Imaging 20:505–515 (1995).

Lohmeyer and Bittman, "Antitumor ether lipids and alklphosphocholines," Drugs of the Future, 19(11):1021–1037 (1994).

Counsell et al., "Synthesis and Evaluation of a Radioiodinated Phospholipid Ether Analog (NM–404) for Diganostic Imaging of Prostate Cancer".

*Primary Examiner*—Floyd D. Higel
*Assistant Examiner*—Golam M. M. Shameem
(74) *Attorney, Agent, or Firm*—Medlen & Carroll, LLP

(57) ABSTRACT

The present invention provides improved radioiodinated phospholipid ether analogs which demonstrate significant tumor avidity and longer plasma half-life than shorter-chain analogs. The radioiodinated phospholipid ether analogs of the present invention provide superior imaging and visualization of neoplastic lesions and tumor-specific cytotoxic cancer therapy.

7 Claims, 8 Drawing Sheets

FIGURE 5A
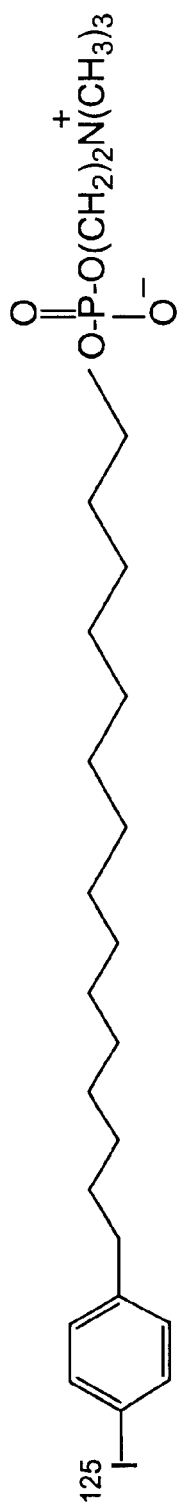
FIGURE 5B
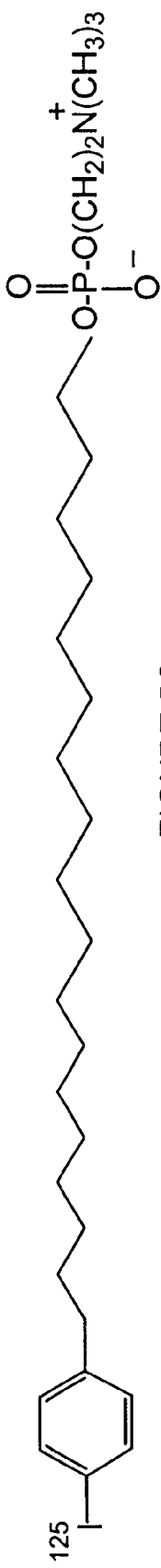
FIGURE 5C
FIGURE 5

FIGURE 7A
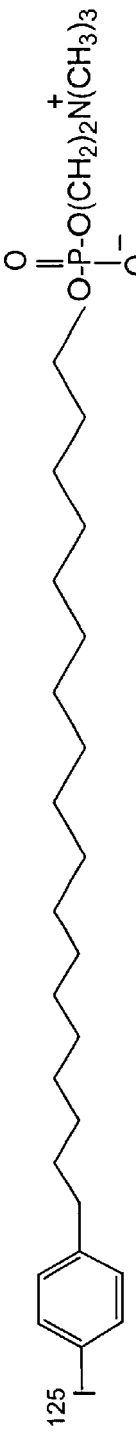
FIGURE 7B
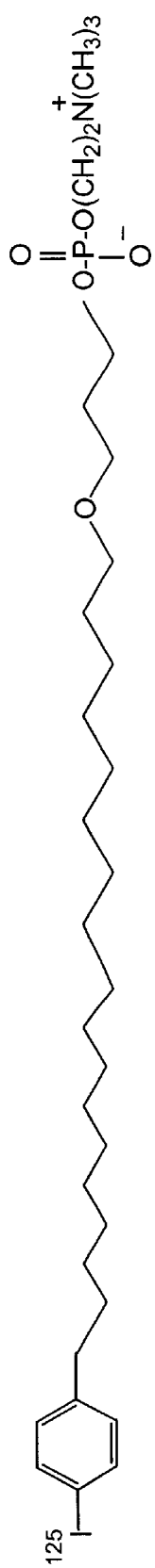
FIGURE 7C
FIGURE 7

RADIOIODINATED PHOSPHOLIPID ETHER ANALOGS AND METHODS OF USING THE SAME

This is a Divisional of application Ser. No. 09/319,406, filed Jun. 4, 1999, now U.S. Pat. No. 6,255,519 which claims benefit under 35 U.S.C. §119 to PCT/US96/19352, filed on Apr. 12, 1999, both of which are herein incorporated by reference in their entirety for all purposes.

This invention was made with government support under grant CA08349 from the National Institutes of Health. The United States Government has certain rights in the invention.

FIELD OF THE INVENTION

The present invention relates generally to the field of radiopharmaceuticals and biological probes, and more specifically to radiolabelled analogs of phospholipid ethers useful in cancer diagnosis and treatment.

BACKGROUND OF THE INVENTION

The early detection of cancer has been one of the primary goals of modern imaging technology, since the identification of a suspected tumor in a localized stage significantly improves the chances for successful treatment and elimination of the cancerous tissue. A large number of imaging strategies have therefore been designed, using a variety of techniques and modalities, to aid the physician in making an accurate diagnosis as early as possible.

Unfortunately, conventional imaging techniques such as computerized tomography (CT) and MRI (magnetic resonance imaging) are limited m their ability to afford a conclusive diagnosis of a suspected lesion, since they are only capable of observing differences in the density or morphology of tissues. A more invasive and costly biopsy procedure is often necessary to provide a definitive diagnosis. In contrast, nuclear medicine techniques such as positron emission tomography (PET) and single photon emission tomography (SPECT) can provide functional or biochemical information about a particular organ or area of interest. However, the success of these nuclear imaging techniques depends in large part on the selective uptake and detection of appropriate radiopharmaceuticals. Selective uptake, in turn, depends upon the development of radiopharmaceuticals with a high degree of specificity for the target tissue. Unfortunately, the tumor-localizing agents developed thus far for oncological applications have had only limited application.

For example, one of these prior art compounds, $^{67}$Ga gallium citrate, was originally identified for its ability to accumulate in tumor tissue. Unfortunately, $^{67}$Ga gallium citrate is taken up by a variety of other non-tumorous lesions as well, including inflammatory lesions, and unacceptable amounts of radioactivity can also accumulate in liver and spleen tissue. The rapid buildup of a radiopharmaceutical in these organs can seriously interfere with the imaging of nearby lesions and also negatively impacts the dosage that can safely be given to a patient.

An alternative approach has been to develop radiolabelled monoclonal antibodies (Mabs) directed to tumor-specific antigens. However, these monoclonal antibodies are specific only to the particular tumor tissue for which they have been produced, and therefore will not localize generally in neoplastic tissue. Moreover, the use of Mabs for diagnostic imaging has lead to additional problems, including varying degrees of antigen expression, low tumor uptake, non-specific binding and adverse immunogenic reactions.

In an attempt to address these problems, the present inventors have recently identified and developed a series of novel compounds demonstrating useful tumor specificity. See, e.g., U.S. Pat. Nos. 4,925,649; 4,965,391; 5,087,721; and 5,347,030; all of which are herein incorporated by reference. It is believed that these radioiodinated phospholipid ether analogs take advantage of a unique biochemical characteristic of malignant tumor cells; i.e. the large concentration of naturally-occurring ether lipids in the cell membranes relative to corresponding normal tissues. Although the precise mechanism of action is not fully understood, the prevailing hypothesis is that the phospholipid ether analogs become entrapped in tumor membranes. Accordingly, these compounds localize in tumor tissue and remain in place for diagnostic and/or therapeutic applications.

The selective retention of the radiolabelled phospholipid ether analogs described in the above patents has been demonstrated in a variety of rodent and animal tumors. Unfortunately, the data obtained from these studies has also demonstrated a relatively rapid clearance of the radiopharmaceutical compound from the blood, and an undesirable accumulation by non-target tissues. As noted above, non-target tissue uptake can decrease the efficacy of radiodiagnostic imaging by creating high background activity, or by causing excessive exposure of radiosensitive tissues to the injected radioactivity.

Accordingly, there remains a significant need in the art for radiopharmaceuticals which exhibit a rapid clearance from non-target tissues as well as an extended half-life in the blood plasma, while still retaining its specificity and avidity for neoplastic tissue. Such an agent should not only assist in the non-invasive imaging of primary tumors and metastases, but should also provide a potential cytotoxic agent for site-specific eradication of the tumor tissue.

SUMMARY OF THE INVENTION

The present invention solves the problems present in the prior art through the provision of improved radiolabelled phospholipid ether analogs of naturally-occurring phospholipid ether compounds, having the general Formula I:

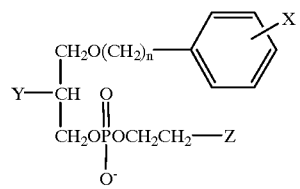

where X is a radioactive isotope and n is an integer between 16 and 30. In a preferred embodiment of the present invention, X is a radioactive isotope of iodine, preferably selected from the group comprising $^{123}$I, $^{125}$I, and $^{131}$I. It is further contemplated that X can be substituted at the ortho, meta or para position on the aromatic ring. In a preferred embodiment, the radioactive isotope is substituted at the para position.

Y is selected from the group comprising H, OH, COOH,

and OR, and Z is selected from the group comprising $NH_2$, $NR_2$, and $NR_3$, wherein R is an alkyl or aralkyl substituent.

In accordance with a specific illustrative embodiment of the invention, the improved compound is 1-O-[18-(p-iodophenyl)octadecyl]-1,3-propanediol-3-phosphocholine.

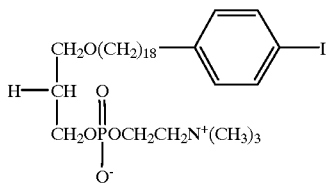

In accordance with another specific illustrative embodiment, the improved compound is 1-O-[18-(p-Iodophenyl)octadecyl]-2-O-methyl-rac-glycero-3-phosphocholine:

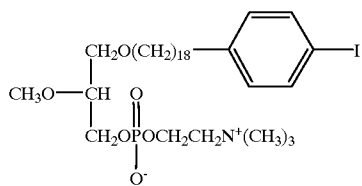

In a further embodiment of the invention, the radiolabelled aralkyl side chain may be substituted directly onto the alkyl phosphocholine moiety in accordance with general Formula II:

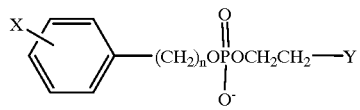

where X is a radioactive isotope substituted at the ortho, meta or para position, preferably of iodine, n is an integer from 16 to 30, and Y is selected from the group comprising $NH_2$, $NR_2$ and $NR_3$, wherein R is an alkyl or aralkyl substituent.

In accordance with a specific illustrative embodiment of the invention, the improved compound is 18-(p-iodophenyl) octadecyl phosphocholine.

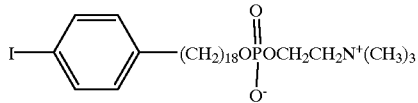

BRIEF DESCRIPTION OF THE FIGURES

FIGS. 5A–5C provide the chemical structures of the alkyl chain length analogs 12-(p-iodophenyl)dodecyl phosphocholine (FIG. 5A), 15-(p-iodophenyl)pentadecyl phosphocholine (FIG. 5B), and 18-(p-iodophenyl)octadecyl phosphocholine (FIG. 5C) used in biodistribution studies with rats bearing Walker-256 tumor;

FIGS. 7A–7C provide the chemical structures of the alkyl chain length analogs 12-(p-iodophenyl)dodecyl phosphocholine (FIG. 7A), 18-(p-iodophenyl)octadecyl phosphocholine (FIG. 7B) and 1-O-[18-(p-iodophenyl)octadecyl]-1,3-propanediol-3-phosphocholine used in biodistribution studies with rats bearing Dunning (MATLyLu) prostate tumors;

GENERAL DESCRIPTION OF THE INVENTION

Figure 1:
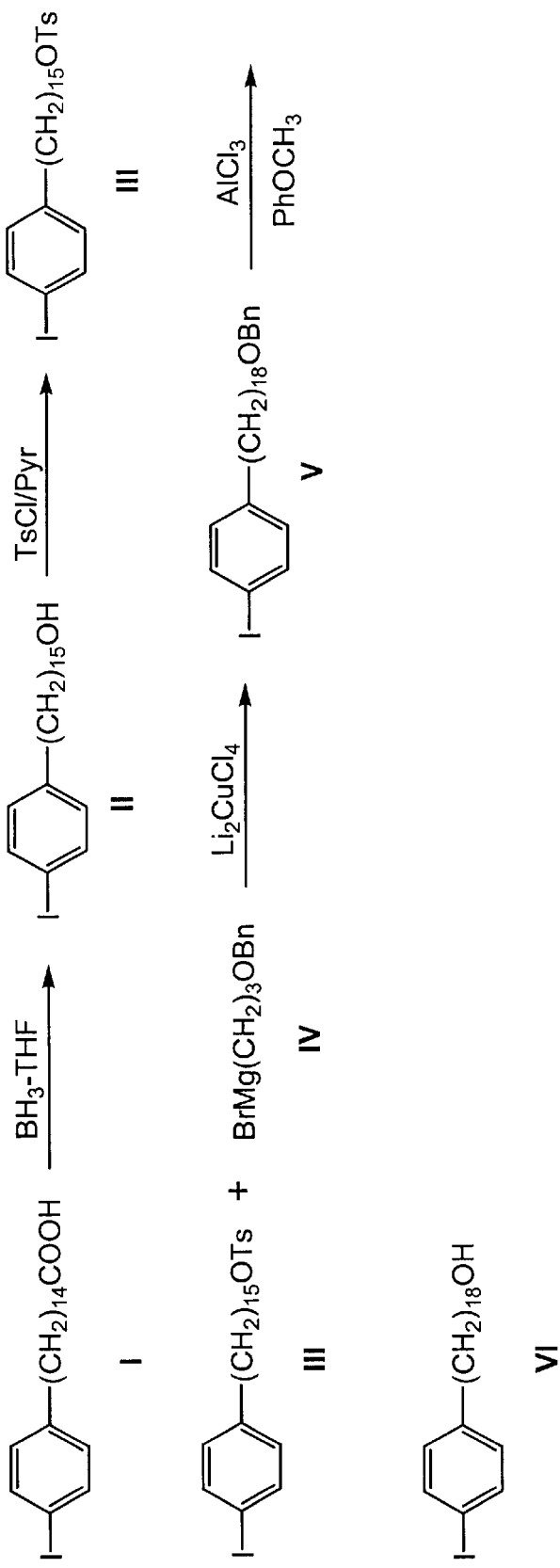
FIG. 1 is an illustrative preparatory scheme for 18-(p-iodophenyl)octadecanol.

The present invention represents a significant improvement of the radiolabelled phospholipid ether analogs previously described in the prior art, providing a series of radiopharmaceutical compounds exhibiting greatly increased plasma half-life and a significantly lower accumulation in non-target organs. Thus, these improved radiopharmaceuticals provide superior tumor imaging capabilities by reducing the amount of background radiation from non-target tissues, and the rapid clearance of the compounds from non-target organs also allows for an increase in the radiation dosimetry of the radiopharmaceutical, for further enhancement of tumor imaging capabilities and cytotoxic cancer therapy.

Surprisingly, the nature of the phospholipid ether compounds which exhibit these enhanced capabilities are compounds having an extension of the carbon chain bearing the radiolabelled phenyl group. Previous studies with related alkyl phosphocholine analogs had demonstrated that blood levels actually decreased with increasing chain length, while tumor levels increased. See, e.g., Kotting et al., "Alkylphosphocholines: influence of structural variation on biodistribution at antineoplastically active concentrations." *Cancer Chemother. Pharm.* 30:105–112 (1992). In contrast, the improved compounds of the present invention have displayed a propensity to remain in the circulation much longer than the original shorter chain analogs, and the delayed clearance from the blood plasma advantageously results in additional opportunities for uptake of the radiopharmaceuticals by tumor tissue as they continuously circulate through the vasculature.

Although an understanding of the underlying mechanism is not essential to the beneficial use of the improved compounds provided by the present invention, the inventors believe that the uptake and transport of the radiolabelled analogs by plasma components may be an important factor relating to the tumor retention of the compounds. Certainly, increasing the length of the carbon chain results in a corresponding increase in the lipophilicity of the analogs, and greater lipophilicity would presumably increase the affinity of these compounds for the cell membrane. There is also evidence (not shown) to indicate that the longer carbon chain alters the binding affinity of these compounds for plasma components such as plasma albumin.

The differences in the clearance and quantity of radioactivity in non-target tissues observed with the improved compounds of the present invention significantly enhances the chances for the imaging of tumors in human patients. Moreover, it should also be noted that the improved phospholipid ether analogs of the present invention are cytotoxic to tumor cells, even without the presence of a radioactive isotope in the compound. Therefore, the inclusion of a long-lived radioactive isotope of iodine, for example, yields tumor-specific radiopharmaceuticals which are tissue-destructive by more than one mode.

DETAILED DESCRIPTION OF THE PREFERRED EMBODIMENTS

The following examples relate to specific embodiments and methods of using the improved radiolabelled phospholipid analogs of the present invention, and include illustrative methods for synthesizing the analogs. All starting materials and reagents were obtained from Aldrich Chemical Company, Milwaukee, Wis.

In the experimental disclosure which follows, the following abbreviations apply: eq (equivalents); M (Molar); $\mu$M (micromolar); N (Normal); mol (moles), mmol (millimoles); $\mu$mol (micromoles): nmol (nanomoles); g (grams); mg (milligrams); kg (kilograms); $\mu$g (micrograms); L (liters); ml (milliliters); $\mu$l (microliters); cm (centimeters); mm (millimeters); $\mu$m (micrometers); nm (nanometers); ° C. (degrees Centigrade); h (hours): min (minutes); sec (seconds): msec (milliseconds); Ci (Curies) mCi (milliCuries); $\mu$Ci (microCuries); TLC (thin layer achromatography); Ts (tosyl); Bn (benzyl); Ph (phenyl); Ms (mesyl); Et (ethyl), Me (methyl).

EXAMPLE 1

The synthesis of 18-(p-Iodophenyl)octadecanol (Compound VI), which is a preliminary compound for the illustrative preparatory schemes for the phospholipid ether analogs discussed in detail in Examples 2 through 4 below, was accomplished from commercially-available 15-(p-iodophenyl)pentadecanoic acid (Compound I) in accordance with the illustrative preparatory scheme shown in FIG. 1.

In general terms, aliphatic chain elongation from C-15 to C-18 was achieved by Li$_2$CuCl$_4$-catalyzed cross-coupling between Grignard reagent (Compound IV) prepared from benzyl 3-bromopropyl ether and 15-(p-iodophenyl) pentadecyl tosylate (Compound III). See, e.g., Fouquet and Schlosser. "Improved carbon-carbon linking by controlled copper catalysis," *Angew. Chem. Int. Ed.* 13:82–83 (1974); Schlosser and Bossert, "The 'two-fold reaction' benchmark applied to the copper catalyzed assembling of 1,ω-difunctional hydrocarbon chains," *Tetrahedron* 47:6287–92 (1991). Cleavage of the benzyl protective group in Compound V by anhydrous aluminum chloride-anisole (see, e.g., Akiyama et al., "AlCl$_3$-N,N-dimethylaniline: a novel benzyl and allyl ether cleavage reagent." *Bull. Chem. Soc. Jpn.* 65:1932–38 (1992)) afforded alcohol VI with 18 carbon atoms in aliphatic chain.

Specifically, to a solution of 15-(piodophenyl)dodecanoic acid (Compound I) (210 mg; 0.47 mmol) in 3 ml of tetrahydrofuran was added BH$_3$.THF complex (1 ml of 1.0 M solution; 1 mmol) dropwise at 0° C. The reaction mixture was then stirred at room temperature under anhydrous conditions for 10 h. It was again cooled to 0° C. and quenched with water. Ethyl acetate and additional water were added. The organic layer was separated, washed with water and dried (Na$_2$SO$_4$). Evaporation of solvent gave the white solid Compound II, 15-(p-iodophenyl)pentadecanol (204 mg, 100%). Compound II was used in the next step without purification.

A mixture of 15-(p-iodophenyl)pentadecanol (Compound II) (200 mg; 0.47 mmol), tosyl chloride (102 mg; 0.53 mmol) and 4-dimethylaminopyridine (66 mg; 0.53 mmol) in dichloromethane (3 ml) was stirred at room temperature for 12 h. The reaction mixture was then partitioned between chloroform (40 ml), methanol (40 ml) and 0.1 N hydrochloric acid (36 ml). The chloroform layer was separated and extraction was repeated (2×40 ml of chloroform). Extracts were combined, dried (Na$_2$SO$_4$) and evaporated. The residue was chromatographed on silica gel in hexane-chloroform (from 95:5 to 40:60) to give Compound III, 15-(p-Iodophenyl)pentadecyl tosylate (259 mg; 95%).

To a solution of 3-benzyloxypropanol (5.28 g; 31.8 mmol) and carbon tetrabromide (3.1 g; 39.6 mmol) in dichloromethane (50 ml) was slowly added triphenylphosphine (10.4 g; 39.7 mmol) at 0° C. The reaction mixture was stirred at 0° C. for 30 min and at room temperature for 1 h. By that time TLC in chloroform showed completion of the reaction. Most of the solvent was evaporated, the residue was diluted with hexane (200 ml) and the precipitate of triphenylphosphinoxide was removed by filtration. Evaporation of the filtrate gave an oily residue which was purified by chromatography in 1% ether in hexane. This afforded Compound IV, benzyl 3-bromopropyl ether (5.61 g; 77%).

To a suspension of magnesium powder (60 mg: 2.5 mmol) in tetrahydrofuran (1.5 ml) was added dibromoethane (0.02 ml) for activation. After the reaction with dibromoethane had ceased, the solution was removed by syringe and replaced with fresh tetrahydrofuran (2.5 ml). Then, benzyl 3-bromopropyl ether (Compound IV) (0.12 ml; 0.67 mmol) was added dropwise to the stirred suspension of magnesium for 30 min. When all the halide had been added, stirring was continued for an additional 2 h at room temperature. The green-gray solution of Grignard reagent was carefully withdrawn by syringe and transferred to 25 ml flask, which was then cooled in a dry ice bath to −78° C. A solution of Li$_2$CuCl$_4$ (0.0067 mmol/ml) in tetrahydrofuran (0.5 ml; 0.0034 mmol) was added to the Grignard reagent under stirring, followed by Compound III, 15-(p-iodophenyl) pentadecyl tosylate (260 mg; 0.44 mmol) in 3 ml of tetrahydrofuran.

The reaction mixture was allowed to warm to room temperature during a 2 h period, and stirring was continued for an additional 12 h. The reaction was quenched by ammonium chloride solution and extracted with ethyl acetate. The extract was washed with water, dried (Na$_2$SO$_4$) and evaporated. Silica gel chromatography with 2% ether in hexane provided Compound V, 1-Benzyloxy-18-(p-iodophenyl)octadecane (190 mg; 76%).

Finally, to a solution of 1-benzyloxy-18-(p-iodophenyl) octadecane (Compound V) (185 mg; 0.33 mmol) and anisole (0.15 ml; 1.32 mmol) in dichloromethane (3 ml) was added anhydrous aluminum chloride (135 mg; 1 mmol) at the room temperature. Stirring was continued for 2 h. The reaction was quenched by diluted hydrochloric acid and extracted by chloroform. Extract was dried (Na$_2$SO$_4$) and evaporated. The residue was chromatographed in hexane-ethyl acetate (gradient from 95:5 to 85:15) to give 18-(p-iodophenyl) octadecanol, Compound VI (123 mg; 77%).

EXAMPLE 2

Further conversion of 18-(p-iodophenyl)octadecanol into the desired phosphocholines was performed as described in detail for the C-12 analogs in Rampy et al., "Synthesis and biological evaluation of radio-iodinated phospholipid ether analogs," *Nucl. Med. Biol.* 22, 505–512 (1995). In one preferred embodiment, the improved phospholipid ether analog contemplated by the present invention is a simple straight chain alkyl phospholipid, 18-(p-iodophenyl) octadecyl phosphocholine (Compound XVI). The synthesis of Compound XVI was accomplished according to the illustrative preparatory scheme shown in FIG. 2.

Figure 2:
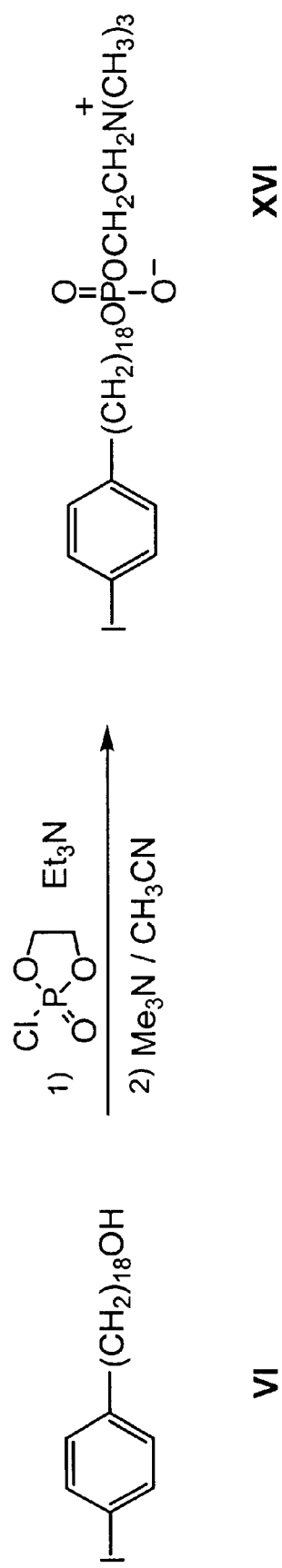
FIG. 2 is an illustrative preparatory scheme for 18-(p-iodophenyl)octadecyl phosphocholine.

As illustrated in FIG. 2, 2-chloro-2-oxo-1,3,2-dioxaphospholane (0.025 ml; 0.27 mmol) was added to the stirred solution of 18-(p-iodophenyl)octadecanol (Compound VI) (115 mg; 0.24 mmol) in dry benzene (3 ml) containing triethylamine (0.042 ml; 0.29 mmol). Stirring was continued overnight. The precipitated triethylamine hydrochloride was filtered off and the solvent was removed in vacuo. The residue was transferred into a pressure bottle. A solution of trimethylamine in acetonitrile (5 ml; 25% w/v) was added. The bottle was sealed and heated at 75° C. for 24 h. The acetonitrile was then evaporated and the residue was chromatographed on silica gel with chloroform-methanol (gradient from 10:0 to 5:5), followed by final elution with chloroform-methanol-water (65:25:4). After evaporation of the solvent, the product was precipitated by addition of acetone to give a white solid (130 mg; 84%).

EXAMPLE 3

Figure 3:
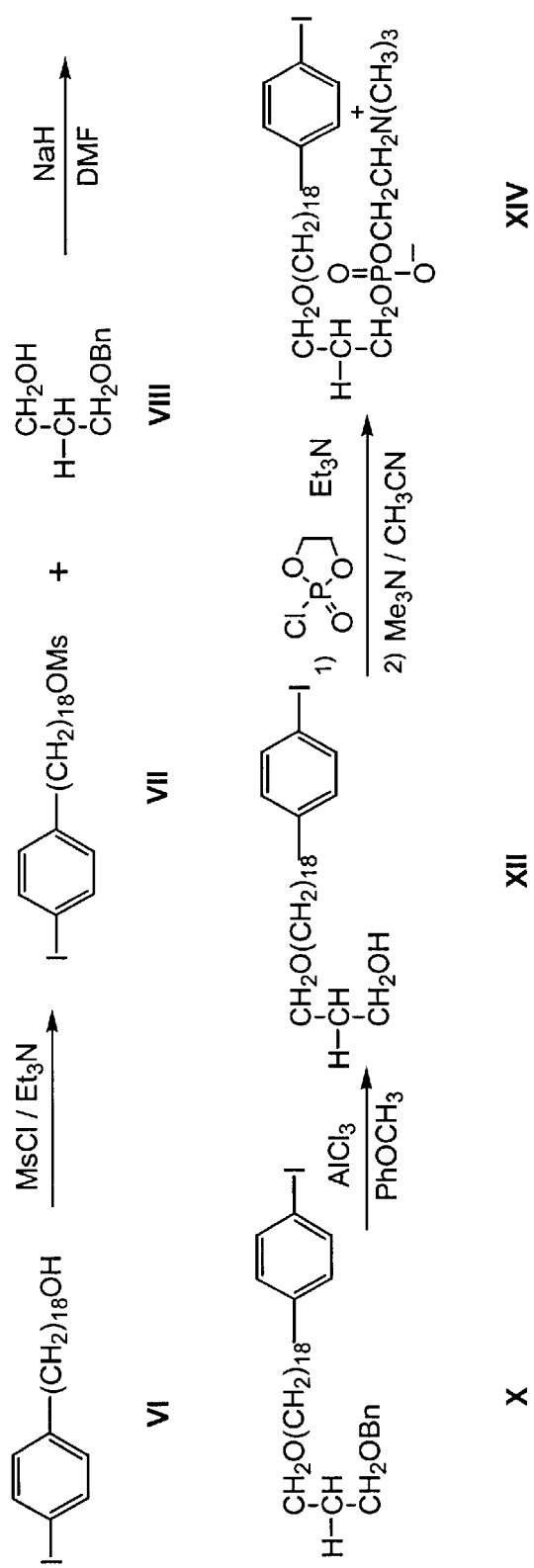
FIG. 3 is an illustrative preparatory scheme for 1-O-[18-(p-iodophenyl)octadecyl]-1,3-propanediol-3-phosphocholine.

In another preferred embodiment, the improved phospholipid ether analogs contemplated by the present invention are constructed using a propanediol backbone. In this example, the synthesis of 1-O-[18-(p-Iodophenyl)octadecyl]-1,3-propanediol-3-phosphocholine (Compound XIV) was accomplished according to the illustrative preparatory scheme shown in FIG. 3.

To a solution of 18-(p-iodophenyl)octadecanol (Compound VI) (150 mg; 0.317 mmol) and triethylamine (0.07 ml; 0.475 mmol) in dry methylene chloride (2 ml) was added methane sulfonyl chloride (0.03 ml: 0.38 mmol) at 0° C. Stirring was continued for 40 min and the reaction was quenched by addition of water. The reaction mixture was diluted with chloroform and washed several times with water. The chloroform layer was dried ($Na_2SO_4$) and evaporated. The residue was chromatographed in hexane-ethyl acetate (9:1). This afforded pure Compound VII, 18-(p-Iodophenyl)octadecyl methanesulfonate (142 mg; 82% yield).

To a solution of 3-benzyloxy propanol (Compound VIII) (0.03 ml; 0.18 mmol) and 18-(p-iodophenyl)octadecyl methanesulfonate (Compound VII) (66 mg: 0.12 mmol) in dry dimethylformamide (3 ml) was added sodium hydride (8 mg of 60% suspension in oil; 0.2 mmol) at the room temperature. The reaction mixture was stirred for 12 hr, quenched by water and extracted with ethyl acetate. The extract was washed with brine, dried and evaporated. Column chromatography in hexane-ethyl acetate (gradient from 95:5 to 85:15) afforded Compound X, 1-O-[18-(p-Iodophenyl) octadecyl]-3-O-benzyl-1,3-propanediol (60 mg; 81% yield).

Compound X was debenzylated by $AlCl_3$-anisole as described for the synthesis of Compound VI, to produce Compound XII, 1-O-[18-(p-Iodophenyl)octadecyl]-1,3-propanediol (50 mg; 0.08 mmol), (42 mg, 99% yield). Finally, the desired phosphocholine XIV was synthesized above from the alcohol XII (42 mg; 79 mmol) in an analogous manner to that described in Example 2 for Compound XVI, (45 mg, 55% yield).

EXAMPLE 4

Figure 4:
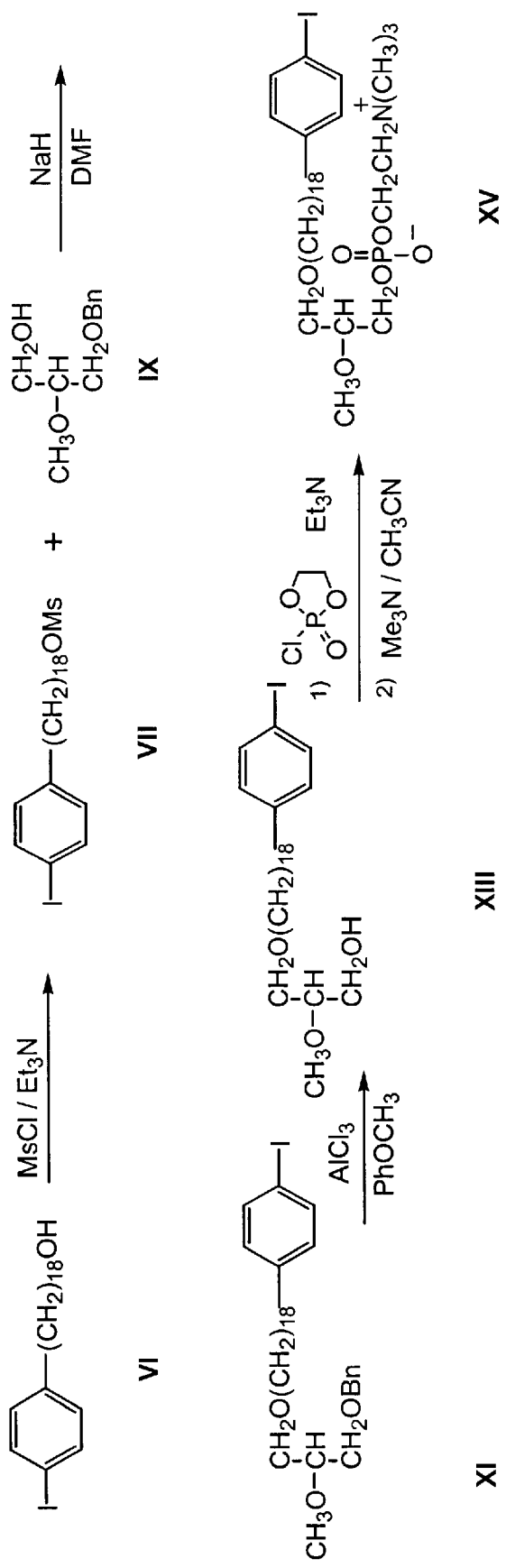
FIG. 4 is an illustrative preparatory scheme for 1-O-[18-(p-iodophenyl)octadecyl]-2-O-methyl-rac-glycero-3-phosphocholine.

This example illustrates yet another preferred embodiment of the improved phospholipid ether analogs contemplated by the present invention, wherein the hydrogen located at the 2-position of Compound XIV is replaced with an O-methyl group. The synthesis of 1-O-[18-(p-Iodophenyl)octadecyl]-2-O-methyl-rac-glycero-3-phosphocholine (Compound XV) was accomplished according to the illustrative preparatory scheme shown in FIG. 4.

Compound XI,1-O-[18-(p-Iodophenyl)octadecyl]-2-O-methyl-3-O-benzyl-rac-glycerol, was synthesized as described above in Example 3 above for Compound X, from 18-(p-iodophenyl)octadecyl methanesulfonate (Compound VII) (67 mg) and 1-O-benzyl-2-O-methyl-rac-glycerol (Compound IX) (36 mg), (62 mg, 78% yield). The synthesis of Compound IX is known in the art and is described in detail in Pinchuk et al., *Chem. Phys. Lipids*, 59:263–65 (1991). Briefly, to 2-O-methyl-1,2-O,O-benzylideneglycerol (2.4 g, 12.4 mmol) cooled in an ice bath was added 18 ml of 1.0 M borane-THF solution (18 ml, 18 mmol) with stirring. After 10 minutes the mixture was left at room temperature for 12 h, then for 48 h at 40–45° C. until TLC (hexane/ethyl acetate 6:4) showed no starting material remained. The mixture was cooled and water was added drop-wise to destroy the borane excess. The solvent was evaporated, the residue was dissolved in water, extracted with ether (3×100 ml), extracts were washed with water, dried ($Na_2SO_4$), and evaporated to give 2.32 g (96%) of a slightly yellow oil. The compound was used for the following step without any further purification.

Compound XIII, 1-O-[18-(p-Iodophenyl)octadecyl]-2-O-methyl-rac-glycerol, was synthesized from the benzyl ether (Compound XI) (58 mg, 0.09 mmol) by the procedure described for Compound VI in Example 1. (40 mg, 80% yield). The desired phosphocholine XV was synthesized from the alcohol XIII (33 mg, 0.06 mmol) by the procedure described in Example 3 above for Compound XVI, (32 mg 75% yield).

EXAMPLE 5

Radioiodination of Phospholipid Ether Analogs

For certain uses, such as scintigraphy or experimental evaluation of tissue distribution, it is desirable to create radioactive compounds. Radioiodination of the iodinated phospholipid ether analogues disclosed herein, or one of the intermediates in the synthesis pathway, can be accomplished by a variety of techniques, some of which are known in the art. For example, aromatic compounds with electron donating groups (such as anilines) can be radiolabelled by electrophilic iodination in the presence of radioiodine, iodine monochloride, chloramine-T, iodogen, etc. Unactivated aromatic rings can be radioiodinated by exchange of a leaving group, such as aryl boronic acids, aryl thallium trifluoroacetates, triazenes or metallated arenes with radioiodine. Direct electrophilic radioiodination of a phenyl ring is yet another alternative, but may produce isomeric mixtures which are difficult to separate. Iodine exhange of aryl iodides with radioiodine may be a preferable approach insofar as no complex separation techniques are necessary, since the substrate and radioiodinated product are chemically identical.

In a preferred embodiment of the invention, an isotope exchange-type technique is utilized wherein the substrate and radioiodine are reacted at an elevated temperature in a "melt." The molten reaction medium possesses a sufficiently high dielectric constant to solubilize both the substrate and radioiodide. Examples of reaction media currently in use are benzoic acid (mp 122° C., bp 249° C.) and acetamide (mp 182° C., bp 221° C.). In a specific preferred embodiment, an acidic exchange medium comprising pivalic acid, a homolog of acetic acid, also known as trimethyl acetic acid, can be used. Pivalic acid has a melting point of 33° C. and a boiling point of 164° C.

The phospholipid ether analogs discussed herein were made via isotope exchange in pivalic acid. This technique is described in detail in Weichert et al., "Radioiodination via isotope exchange in pivalic acid," *Appl. Radiat. Isot.* 37:907–13 (1986). Briefly, the unlabeled compound (0.5 mg) was placed in a 300-$\mu$l V-vial (Wheaton, Millville, N.J.) fitted with teflon faced seal and screw cap. Absolute ethanol (20 $\mu$l) was added via a microliter syringe, followed by aqueous Na$^{125}$I (0.5–3.0 mCi, 2–10 $\mu$l) (no-carrier-added in reductant-free 0.1 N NaOH from Amersham Radiochemicals). The vial was gently swirled to dissolve the contents and ensure homogeneity.

Inlet and outlet cannuli were inserted and a gentle stream of nitrogen was applied to remove the solvents. Two successive in-line charcoal traps were placed on the outlet side in order to trap any volatile radioiodine present in the reaction vial. Once dry, solid pivalic acid (5 mg), previously dried by azeotropic removal of water with toluene and distilled under nitrogen was added. The vial was sealed and heated at 160° C. in a preheated single well aluminum heating block containing 1 cm of sand in the bottom of the well. After 1 hr., the reaction vial was removed from the heating block and allowed to cool to room temperature. Absolute ethanol (70 $\mu$l) was added through a micro syringe followed by gentle agitation and subsequent removal of a TLC sample (1–2 $\mu$l).

The entire contents of the reaction vial were then injected directly onto a silica gel HPLC column eluted with hexane/isopropanol/water (40:52:8) at 0.8 ml/min. Peaks were analyzed by both UV (230 and 254 mn) and radiodetection. After pooling appropriate fractions the radiochemical purity of the final product was monitored by TLC (gamma and UV detection) and by HPLC (UV at 230254 nm and radiochemical detector). Fractions were combined and the solvent was removed with a gentle stream of nitrogen. HPLC analysis of the final compound confirmed both chemical (UV at 230/254 nm) and radiochemical (radioactivity) purity.

Of course, any isotope of iodine such as the clinically used isotopes, $^{122}$I, $^{123}$I, $^{125}$I and $^{131}$I can be used. $^{125}$I is preferred for in vitro work in the laboratory due to its relatively long half-life. For radiodiagnostic purposes in humans, $^{123}$I or $^{131}$I are preferred due to their shorter half-lives and favorable imaging energies. Thus, the radioiodination procedure described above may be modified, as known by those of skill in the art, to compensate for the difference in half-life.

It is further contemplated that the radioiodinated phospholipid ether analogs of the present invention may be solubilized in a suitable transport agent or carrier vehicle, and administered to mammalian subjects as radiologic agents by any known manner, preferably parentally such as intravenously or intraperitonally. It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Oral formulations for cancer usually will include such normally employed additives such as binders, fillers carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compositions are also prepared as injectables, either as liquid solutions or suspensions; solid forms suitable for solution in, or suspension in, liquid prior to injection may also be prepared. The radioiodinated compounds of the present invention are often mixed with diluents or excipients which are physiologically tolerable and compatible. Suitable diluents and excipients are, for example, water, saline, dextrose glycerol, or the like, and combinations thereof. In addition if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

EXAMPLE 6

Biodistribution Studies with Walker-256 Carcinosarcoma

The three radiolabelled compounds illustrated in FIG. 5, including the improved C-18 analog 18-(p-iodophenyl) octadecyl phosphocholine (Compound XVI) described in Example 2, were prepared and administered to two sets of female Sprague Dawley rats (Charles River, Portage, Mich.). One normal set was used as a control, and one set was inoculated with Walker-256 carcinosarcoma cells ($5 \times 10^6$ cells) in 0.2 ml saline in the right hindlimb. The Walker carcinoma cell line was provided by Dr. James Varani of the Department of Pathology at the University of Michigan, and is an accepted cell line representative of effect in humans. See, e.g. Tayck et al., "Influence of the Walker 256 Carcinosarcoma on Muscle, Tumor, and Whole-Body Protein Synthesis and Growth Rate in the Cancer-Bearing Rat, *Cancer Res.* 46:5649–54 (1986).

The animals were used 6–8 days later when the tumor weight averaged 10 g. The radiolabelled compounds were dissolved in absolute ethanol (50–500 $\mu$l) and Tween-20 (0.1 ml/mg of compound) was added to the solution. Ethanol was removed by evaporation under a stream of nitrogen. Physiological saline or sterile water was added, to give a 2–3% Tween-20 solution which was subsequently mixed by vortex. The solubilized radiolabelled compounds (5–10 $\mu$Ci, 0.3 ml) were administered intravenously via the tail vein to tumor bearing rats, and the animals were sacrificed by exsanguination while under ether anesthesia at the various time points. Blood samples were collected through cardiac puncture and selected tissues (liver, kidney, etc.) were removed, trimmed, blotted to remove excess blood and weighed. Large organs were thoroughly minced with scissors to obtain random representative tissue samples.

For the biodistribution experiments with 12-(p-iodophenyl)dodecyl phosphocholine, weighed tissue samples were counted with a well scintillation counter (85% counting efficiency). The concentration of radioactivity in each tissue was expressed as a percentage of administered dose per gram of tissue.

Tissue distribution was assessed at various times following administration of the radioiodinated chain length isomers. An illustration of the data for each analog is set forth in Table 1 below. The results are expressed as the mean % administered dose per gram±SEM (% Dose/g±SEM).

|  | C-12 Analog | | C-15 Analog | | C-18 Analog | |
|---|---|---|---|---|---|---|
| Tissue | 24 hr | 48 hr | 24 hr | 48 hr | 24 hr | 48 hr |
| Adrenal | 0.33 ± 0.01 | 0.29 ± 0.01 | 0.73 ± 0.08 | 0.49 ± 0.05 | 0.85 ± 0.04 | 0.92 ± 0.06 |
| Blood | 0.27 ± 0.04 | 0.27 ± 0.03 | 0.16 ± 0.01 | 0.14 ± 0.01 | 0.96 ± 0.00 | 0.64 ± 0.07 |
| Duodenum | 1.35 ± 0.13 | 0.77 ± 0.06 | 1.13 ± 0.13 | 1.38 ± 0.24 | 0.69 ± 0.05 | 0.68 ± 0.04 |
| Kidney | 4.10 ± 0.44 | 3.44 ± 0.08 | 1.14 ± 0.11 | 0.91 ± 0.04 | 0.65 ± 0.00 | 0.59 ± 0.04 |
| Liver | 1.62 ± 0.17 | 1.37 ± 0.01 | 1.29 ± 0.10 | 0.83 ± 0.04 | 0.55 ± 0.04 | 0.59 ± 0.05 |
| Lung | 1.06 ± 0.04 | 0.53 ± 0.01 | 0.97 ± 0.03 | 0.81 ± 0.04 | 0.88 ± 0.06 | 0.76 ± 0.07 |
| Plasma | 0.39 ± 0.05 | 0.39 ± 0.05 | 0.16 ± 0.01 | 0.15 ± 0.03 | 1.47 ± 0.03 | 0.95 ± 0.11 |
| Tumor | 2.99 ± 0.34 | 1.84 ± 0.09 | 1.47 ± 0.10 | 1.65 ± 0.23 | 0.98 ± 0.07 | 1.14 ± 0.01 |

Figure 6:
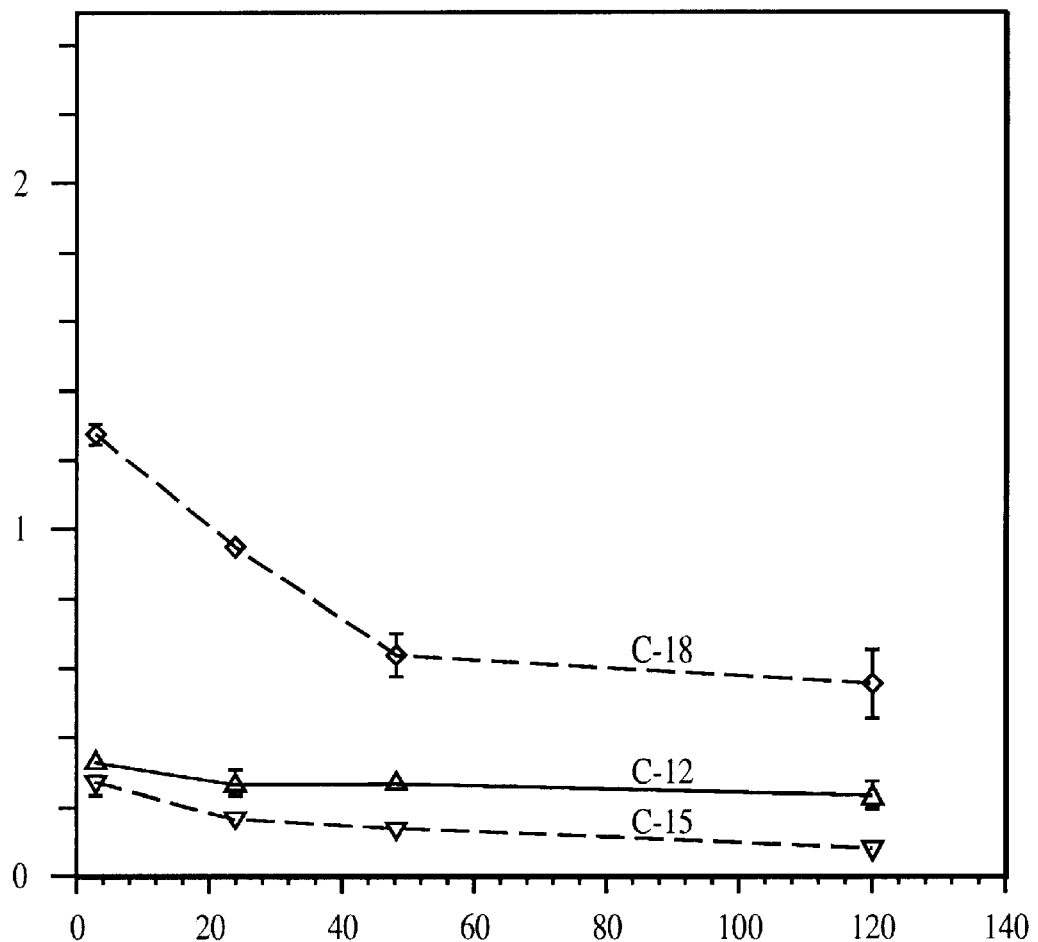
FIG. 6 provides a line graph illustrating the blood clearance profile of 12-(p-iodophenyl)dodecyl phosphocholine (C-12), 15-(p-iodophenyl)pentadecyl phosphocholine (C-15) and 18-(p-iodophenyl)dodecylphosphocholine (C-18) in rats bearing Walker-256 tumors.

As the above data clearly demonstrates, the clearance of the C18 analog from non-target tissues was much more rapid than from tumor, and the quantities of radioactivity detected in the liver, kidney and duodenum were significantly lower following administration of the C18 analog, as compared to the same organs in the C15 and C12 analog studies. In addition, the C18 analog was retained in the circulation to a much greater extent than the other chain length isomers surveyed. As Table 1 illustrates, the plasma level for the C-18 analog was significantly higher than the plasma levels for both the C-12 and the C-15 analog. Moreover, even at 120 hours, blood levels for the C18 analog were 0.60±0.01 (% Dose/g±SEM), as compared to levels of 0.07±0.01 and 0.22±0.03 for the C15 and C12 analogs, respectively. This effect is illustrated in FIG. 6, which shows the blood clearance profile of all three analogs up to 120 hours post-injection.

While the rapid decline in radiation levels in non-target tissue was accompanied by a much more subtle reduction in the radioactivity present in the tumor, the C18 analog still retained a beneficial degree of tumor specificity in this tumor model. In fact, the level of C18 in the tumor increased significantly over a longer time period, most likely as a result of the longer plasma half-life.

EXAMPLE 7

Biodistribution Studies with Dunning Prostate Tumor

The three radiolabelled compounds illustrated in FIGS. 7A–7C, including the improved C-18 analogs 18-(p-iodophenyl)octadecyl phosphocholine (Compound XVI—FIG. 7B) and 1-O-[18-(p-iodophenyl)octadecyl]-1,3-propanediol-3-phosphocholine (Compound XIV—FIG. 7C) described in Examples 2 and 3, respectively, were prepared and administered to two sets of male Copenhagen rats (Harlan Sprague-Dawley, Indianapolis, Ind.). One group of normal animals was used as a control, and another group was inoculated with Dunning prostate tumor cells ($1\times10^6$ MAT-LyLu cells) in 0.2 ml saline in the right hindlimb. The MAT-LyLu subline of the Dunning (R-3327) adenocarcinoma prostate tumor was provided by Dr. Ken Pienta of the Department of Urology at the University of Michigan, and is an accepted cell line representative of effect in humans. See, e.g., Pienta et al., "Inhibition of Spontaneous Metastasis in a Rat Prostrate Cancer Model by Oral Administration of Modified Citrus Pectin, *J. Natl. Cancer Inst.* 87:348–53 (1995).

The animals were maintained with free access to food and water until day 8–10. The radioiodinated phospholipid ether analog formulated in 2% Tween 20—sterile water (5–10 $\mu$Ci, 0.3–0.4 ml, described above in Example 6) was administered intravenously into the tail vein of the tumor-bearing animals under metofane anesthesia. The animals were euthanized at selected time points after injection (n=3 per time point) and samples of blood, plasma and a variety of tissues including tumor and prostate are collected and analyzed for radioiodine content. Biodistribution values are calculated as the mean of the individual % administered dose per gram of tissue and % dose per organ values. An illustration of the data for each analog is set forth in Table 2 below. These results are also expressed as the mean % administered dose per gram±SEM (% Dose/g±SEM).

|  | C-12 Analog | | Compound XIV | | Compound XVI | |
|---|---|---|---|---|---|---|
| Tissue | 24 hr | 48 hr | 24 hr | 48 hr | 24 hr | 48 hr |
| Adrenal | 0.29 ± 0.01 | 0.23 ± 0.01 | 1.37 ± 0.03 | 1.04 ± 0.07 | 0.88 ± 0.02 | 0.76 ± 0.03 |
| Blood | 0.23 ± 0.02 | 0.22 ± 0.01 | 0.41 ± 0.01 | 0.29 ± 0.01 | 0.88 ± 0.04 | 0.64 ± 0.05 |
| Kidney | 4.45 ± 0.27 | 3.38 ± 0.43 | 0.73 ± 0.02 | 0.65 ± 0.01 | 0.59 ± 0.02 | 0.51 ± 0.03 |
| Liver | 1.27 ± 0.02 | 1.05 ± 0.03 | 0.57 ± 0.02 | 0.36 ± 0.01 | 0.57 ± 0.02 | 0.40 ± 0.03 |
| Lung | 0.48 ± 0.03 | 0.33 ± 0.02 | 0.89 ± 0.07 | 0.78 ± 0.02 | 0.84 ± 0.01 | 0.69 ± 0.05 |

-continued

| | C-12 Analog | | Compound XIV | | Compound XVI | |
|---|---|---|---|---|---|---|
| Tissue | 24 hr | 48 hr | 24 hr | 48 hr | 24 hr | 48 hr |
| Plasma | 0.32 ± 0.03 | 0.32 ± 0.01 | 0.58 ± 0.01 | 0.42 ± 0.03 | 1.43 ± 0.06 | 0.99 ± 0.11 |
| Tumor | 0.37 ± 0.03 | 0.30 ± 0.01 | 0.43 ± 0.05 | 0.39 ± 0.01 | 0.75 ± 0.04 | 0.81 ± 0.04 |

As with the Walker-256 tumor in Example 6, the C-18 analogs again demonstrated kidney and liver levels several times lower than the C-12 analog in the prostate tumor model. Importantly, however, the longer chain analogs also demonstrated a superior tumor avidity, with tumor levels of Compound XVI more than twice as high as the shorter chain analog. Thus, the improved compounds of the present invention may find particularly advantageous use in the imaging and/or treatment of prostate tumors.

EXAMPLE 8

Gamma Camera Scintigraphy Studies with Dunning R3327 Prostate Tumor

Comparative in vivo scintigaphic studies were also conducted using the C-12 analog 12-(p-iodophenyl)dodecyl phosphocholine and the C-18 analogs 18-(p-iodophenyl) octadecyl phosphocholine (Compound XVI) and 1-O-[18-(p-iodophenyl)octadecyl]-1,3-propanediol-3-phosphocholine (Compound XIV) utilized in Example 7. The imaging studies were performed on Dunning R3327 prostate tumor-bearing animals injected with >40 $\mu$Ci of the radioiodinated phospholipid ether formulations described above. The anesthetized animals were imaged at selected times after injection on a gamma camera set to the $^{125}$I window and outfitted with a low energy collimator. Static fifteen-minute images were obtained for each animal at the specified time. The results are illustrated in FIGS. 8A–8C.

Figure 8A:
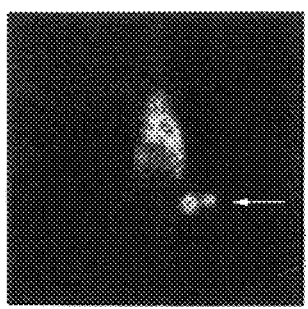
FIGS. 8A–8C are depictions of whole-body gamma-camera scintigraphy scans of Dunning (MATLyLu) prostate tumor-bearing using 18-(p-iodophenyl)octadecyl phosphocholine (FIG. 8A), 12-(p-iodophenyl)dodecyl phosphocholine (FIG. 8B) and 1-O-[18-(p-iodophenyl)octadecyl]-1,3-propanediol-3-phosphocholine (FIG. 8C).
Figure 8B:
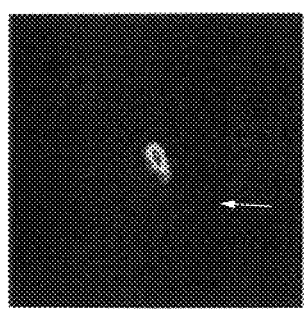
Figure 8C:
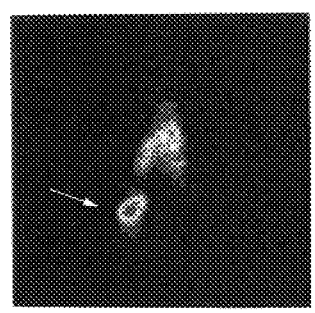

As illustrated in FIGS. 8A–8C for 18-(p-iodophenyl) octadecyl phosphocholine (Compound XVI), 12-(p-iodophenyl)dodecyl phosphocholine and 1-O-[18-(p-iodophenyl)octadecyl]-1,3-propanediol-3-phosphocholine (Compound XIV), respectively, the mass designated as T corresponds to the tumor tissue. Administration of the C-18 compounds resulted in excellent tumor localization in comparison with the C-12 analog, wherein the tumor was barely visible.

In addition to the foregoing specifically mentioned uses of the inventive compounds, the compounds of the present invention may find applicability as carrier molecules for radiosensitizers. Radiosensitizers are agents administered to sensitize tumor tissue to the effects of externally applied radiation. Well known radiosensitizers, such as misonidazole and metronidazole are substituted nitroimidazoles. Substitution of an electron-capturing moiety, such as nitroimidazole, for the iodophenyl moiety in the phospholipid ether analogues of the present invention would permit tumor-localized sensitization for radiation therapy.

In yet another proposed use, the phospholipid analogues of the present invention could incorporate boron containing substituents for use as boron-neutron activation therapeutic agents. These therapeutic agents are administered using the stable isotope of the electron-capturing boron. External radiation activates the boron to create tissue destructive activity.

Although the invention has been described in terms of specific embodiments and applications, persons skilled in this art can, in light of this teaching, generate additional embodiments without exceeding the scope or departing from the spirit of the claimed invention. In particular, the methods of synthesis are merely illustrative and can be modified by those of skill in the art for the production of various substituted phospholipid ether analogues in accordance with the invention. Moreover, other techniques of radio-tagging the analogues may be employed. Of course, the invention contemplates any one of the ortho-, meta- and para-isomers of iodobenzyl as the iodine-bearing moiety.

In addition, while certain preferred embodiments of the improved phosphilipid ether analogs described herein incorporate an 18-carbon alkyl chain into the compound, both longer and shorter chains are also contemplated to be within the scope of the present invention. In their association with the plasma membrane of cells, the long aliphatic chain of the phospholipid ether analogs of the present invention presumably become buried in the hydrophobic phospholipid bilayer. Both NMR and x-ray diffraction studies have shown that the thickness of this hydrophobic phase of the lipid bilayer is between 35 and 40 Angstroms depending on the type of phospholipid making up the membrane. See Yeagle, P., Ed., "The Structure of Biological Membranes," page 345, CRC Press, Boca Raton, Fla. (1991). Accordingly, based on the expectation that hydrophobic chains as long as 40 Angstroms can be expected to intercalate into such lipid bilayers, the present invention contemplates that the extended alkyl chain can be up to 30 carbons in length.

Accordingly, it is to be understood that the drawings and descriptions in this disclosure are proffered to facilitate the comprehension of the invention and should not be construed to limit the scope thereof. Other improvements and modifications which become apparent to persons of ordinary skill in the art only after reading this disclosure, the drawings and the following claims are deemed within the spirit and scope of the present invention.

We claim:

1. A compound of the general formula:

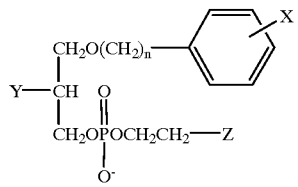

where X is a radioactive isotope of iodine; n is an integer between 16 and 30; Y is selected from the group consisting of H, OH, COOH,

and OR, and Z is selected from the group consisting of $NH_2$, $NR_2$, and $NR_3$, wherein R is an alkyl or aralkyl substituent.

2. The compound of claim 1 wherein X is a radioactive isotope of iodine consisting of $^{123}$I, $^{125}$I, or $^{131}$I.

3. A method of radio imaging a host, comprising the steps of administering to the body of said host an effective amount of a radiopharmaceutical compound as claimed in claim 1 and subsequently scanning said host.

4. 1-O-[18-(p-Iodophenyl)octadecyl]-1,3-propanediol-3-phosphocholine, wherein iodine is in the form of a radioactive isotope.

5. The compound of claim 4 wherein the radioactive isotope of iodine is selected from the group consisting of $^{123}$I, $^{125}$I, and $^{131}$I.

6. 1-O-[18-(p-Iodophenyl)octadecyl]-2-O-methyl-rac-glycero-3-phosphocholine, wherein iodine is in the form of a radioactive isotope.

7. The compound of claim 6 wherein the radioactive isotope of iodine is selected from the group consisting of $^{123}$I, $^{125}$I, and $^{131}$I.

* * * * *

UNITED STATES PATENT AND TRADEMARK OFFICE
CERTIFICATE OF CORRECTION

PATENT NO. : 6,417,384 B1
APPLICATION NO. : 09/898178
DATED : July 9, 2002
INVENTOR(S) : Counsell et al.

Page 1 of 1

It is certified that error appears in the above-identified patent and that said Letters Patent is hereby corrected as shown below:

Please amend the Specification at Claim 1, column 14, line 67 in the following manner:

~~$NR_2$, and $NR_3$~~ $N(R)_2$, and $N(R)_3$, wherein R is an alkyl or aralkyl substituent.

Signed and Sealed this

Nineteenth Day of May, 2009

JOHN DOLL
*Acting Director of the United States Patent and Trademark Office*

UNITED STATES PATENT AND TRADEMARK OFFICE
CERTIFICATE OF CORRECTION

PATENT NO. : 6,417,384 B1
APPLICATION NO. : 09/898178
DATED : July 9, 2002
INVENTOR(S) : Counsell et al.

It is certified that error appears in the above-identified patent and that said Letters Patent is hereby corrected as shown below:

Please amend the Specification at column 2, line 67 in the following manner:

~~NR$_2$ and NR$_3$~~ N(R)$_2$, and N(R)$_3$, wherein R is an alkyl or aralkyl substituent.

Please amend the Specification at column 3, line 41 in the following manner:

NH$_2$, ~~NR$_2$ and NR$_3$~~ N(R)$_2$, and N(R)$_3$, wherein R is an alkyl or aralkyl.

Signed and Sealed this

Fifteenth Day of September, 2009

David J. Kappos
*Director of the United States Patent and Trademark Office*